United States Patent [19]

Scherkenbeck et al.

[11] Patent Number: 5,874,530
[45] Date of Patent: Feb. 23, 1999

[54] CYCLIC DEPSIPEPTIDE SULFONYLATION, SULFENYLATION AND PHOSPHORYLATION PROCESS

[75] Inventors: Jürgen Scherkenbeck, Wermelskirchen; Andrew Plant; Peter Jeschke, both of Leverkusen; Achim Harder, Köln; Norbert Mencke, Leverkusen, all of Germany

[73] Assignee: Bayer Aktiengesellschaft, Leverkusen, Germany

[21] Appl. No.: 817,279

[22] PCT Filed: Oct. 5, 1995

[86] PCT No.: PCT/EP95/03926

§ 371 Date: Apr. 10, 1997

§ 102(e) Date: Apr. 10, 1997

[87] PCT Pub. No.: WO96/11945

PCT Pub. Date: Apr. 25, 1996

[30] Foreign Application Priority Data

Oct. 18, 1994 [DE] Germany .................. 44 37 198.5

[51] Int. Cl.⁶ .................. C07K 5/12; A61K 37/02; A61K 38/00
[52] U.S. Cl. .................. 530/317; 514/9; 514/11; 530/345
[58] Field of Search .................. 530/317, 345; 514/9, 11

[56] References Cited

U.S. PATENT DOCUMENTS 5,116,815  5/1992  Takagi et al. .................. 514/11

FOREIGN PATENT DOCUMENTS 0382173  8/1990  European Pat. Off. .
0626376  5/1994  European Pat. Off. .
9611945  4/1996  WIPO .

OTHER PUBLICATIONS

Proceedings of Nobel Symposium, vol. 34, 1976, Stockholm, pp. 345–372, XP002005330, Yu. A. Ovchinnikov, "Recent Findings in the Structural and Functional Aspects of the Peptide Ionophores".

Shimohigashi et al, *Cyclic Peptide*, Int. J. Peptide Protein Res. 12, pp. 7–16, 1978.

*Primary Examiner*—Cecilia J. Tsang
*Assistant Examiner*—S. G. Marshall
*Attorney, Agent, or Firm*—Sprung Kramer Schaefer & Briscoe

[57] ABSTRACT

The present invention relates to a process for the aromatic sulfonylation, sulfenylation, thiocyanation and phosphorylation of cyclic depsipeptides having 6 to 24 ring atoms which are synthesized from α-hydroxycarboxylic acids and α-amino acids and contain at least one phenyl radical, characterized in that these cyclic depsipeptides are reacted with sulfonylating, sulfenylating, thiocyanating or phosphorylating agents, optionally in the presence of catalysts, auxiliaries and/or diluents, to novel thus-obtained compounds, and to their use as endoparasiticides.

20 Claims, No Drawings

CYCLIC DEPSIPEPTIDE SULFONYLATION, SULFENYLATION AND PHOSPHORYLATION PROCESS

This application is a 371 of PCT/EP95/03926 filed Oct. 5, 1995.

The present invention relates to a process for the sulfonylation, sulfenylation, thiocyanation and phosphorylation of cyclic depsipeptides, to novel compounds and their use as endoparasiticides.

Cyclic depsipeptides and their action as endoparasiticides are already known from EP 381 173, PCT WO 93/19 053. However, the activity of these compounds is not always satisfactory.

The present invention relates to

1. The process for the aromatic sulfonylation, sulfenylation, thiocyanation and phosphorylation of cyclic depsipeptides having 6 to 24 ring atoms which are synthesized from α-hydroxycarboxylic acids and α-amino acids and contain at least one phenyl radical, characterized in that these cyclic depsipeptides are reacted with sulfonylating, sulfenylating, thiocyanating or phosphorylating agents, optionally in the presence of catalysts, auxiliaries and/or diluents.

2. Aromatically sulfonylated, sulfenylated, thiocyanated and/or phosphorylated cyclic depsipeptides having 6 to 24 ring atoms which are synthesized from α-hydroxycarboxylic acids and α-amino acids and contain at least one phenyl radical.

Cyclic depsipeptides, which are employed as starting materials in the process according to the invention, are natural compounds usually prepared by fermentation. Structurally, they are similar to proteins. Therefore, they would be expected to be sensitive toward aggressive chemicals and to be destroyed entirely or at least partially. Surprisingly, it was found that the process according to the invention can be carried out without destroying the basic structure of the depsipeptides. Compounds are thus obtained which are sulfonylated, sulfenylated, thiocyanated or phosphorylated on the phenyl ring and which have outstanding endoparasiticidal activity.

The process according to the invention is preferably employed for preparing the novel and preferred compounds of the formula (I)

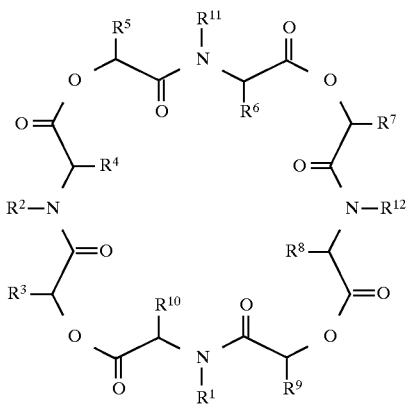

as the core structure and in which at least one of the radicals $R^3, R^4, R^5, R^6, R^7, R^8, R^9$ or $R^{10}$ represents phenyl or benzyl, each of which is substituted by a sulfonyl, sulfenyl, thiocyanato or phosphoryl radical
and in which otherwise the radicals $R^1, R^2, R^{11}$ and $R^{12}$ each represent hydrogen or optionally substituted $C_{1-8}$-alkyl, $C_{3-6}$-cycloalkyl, aralkyl or aryl radicals, $R^3, R^5, R^7$ and $R^9$ each represent hydrogen, straight-chain or branched $C_{1-8}$-alkyl which is optionally substituted by hydroxyl, $C_{1-4}$-alkoxy, aryloxy, hetaryloxy, carboxyl,

carboxamide,

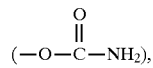

imidazolyl, indolyl, guanidino, —SH or $C_{1-4}$alkylthio, and further represent optionally substituted aryl, hetaryl or aralkyl, $R^4, R^6, R^8$ and $R^{10}$ each represent hydrogen, straight-chain or branched $C_{1-8}$-alkyl, $C_{2-6}$-alkenyl or $C_{3-7}$-cycloalkyl, each of which is optionally substituted by hydroxyl, $C_{1-4}$-alkoxy, carbonyl, carboxamide, imidazolyl, indolyl, guanidino, SH or $C_{1-4}$-alkylthio, or represent optionally substituted aryl, hetaryl or aralkyl.

Particularly preferred are compounds of the formula (I) in which at least one of the radicals $R^3$ to $R^{10}$ represents benzyl which is substituted by a sulfonyl, sulfenyl, thiocyanato or phosphoryl radical and in which otherwise the radicals have the meanings stated above.

Particularly preferred are compounds of the formula (I) in which one or both of the radicals $R^3$ and $R^7$ represent benzyl which is substituted by a sulfonyl, sulfenyl, thiocyanato or phosphoryl radical and in which otherwise the radicals have the meanings stated above.

Suitable sulfonyl, sulfenyl, thiocyanato or phosphoryl radicals are:

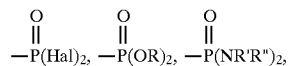

—SO$_2$ —A; —SO—A, —S—A SCN, wherein

| | |
|---|---|
| Hal | represents halogen, |
| A | represents halogen, hydroxyl, —OR, —NH$_2$, —NHR', —NR'R", |
| R | represents optionally substituted alkyl, alkenyl, alkinyl, aryl or aralkyl, |
| R' | represents optionally substituted alkyl, aryl or aralkyl, |
| R" | represents optionally substituted alkyl, aryl, or aralkyl, | and the radicals R' and R" represent together with the nitrogen atom attached an optionally substituted heterocyclic radical which may contain further heteroatoms such as N, 0 or S.

In the general formulae, optionally substituted alkyl on its own or as part of a radical is straight-chain or branched alkyl having preferably 1 to 8, in particular 1 to 5 carbon atoms. Preferred examples are optionally substituted methyl, ethyl, n- and i-propyl, n-, i- and t-butyl.

In the general formulae, optionally substituted alkenyl on its own or as part of a radical is straight-chain or branched alkenyl having preferably 2 to 6, in particular 2 to 4 carbon atoms. Preferred examples are optionally substituted ethenyl, 1-propenyl, 2-propenyl and 3-butenyl.

In the general formulae, optionally substituted cycloalkyl is mono-, bi- and tricyclic cycloalkyl having preferably 3 to 6, in particular 3, 5 or 6 carbon atoms. Preferred examples are optionally substituted cyclopropyl, cyclobutyl, cyclopentyl and cyclohexyl.

In the general formulae, optionally substituted alkoxy is straight-chain or branched alkoxy having preferably 1 to 6, in particular 1 to 4 carbon atoms. Preferred examples are optionally substituted methoxy, ethoxy, n- and i-propoxy and n-, i- and t-butoxy.

In the general formulae, optionally substituted alkylthio is straight-chain or branched alkylthio having preferably 1 to 6, in particular 1 to 4 carbon atoms. Preferred examples are optionally substituted methylthio, ethylthio, n- and i-propylthio, n-, i- and t-butylthio.

In the general formulae, halogenoalkyl contains 1 to 4, in particular 1 or 2 carbon atoms and preferably 1 to 9, in particular 1 to 5 identical or different halogen atoms, preferred halogen atoms being fluorine, chlorine and bromine in particular fluorine and chlorine. Examples are trifluoromethyl, chloro-di-fluoromethyl, 2,2,2-trifluoroethyl and pentafluoroethyl, and perfluoro-t-butyl.

In the general formulae, optionally substituted aryl is preferably optionally substituted phenyl or naphthyl, in particular phenyl.

In the general formulae, optionally substituted aralkyl is aralkyl optionally substituted in the aryl moiety and/or alkyl moiety having preferably 6 or 10, in particular 6 carbon atoms in the aryl moiety (preferably phenyl or naphthyl, in particular phenyl) and preferably 1 to 4, in particular 1 or 2 carbon atoms in the alkyl moiety, the alkyl moiety being straight-chain or branched. Preferred examples are optionally substituted benzyl and phenylethyl.

In the general formulae, optionally substituted hetaryl on its own or as part of a radical is a 5- to 7-membered ring having preferably 1 to 3, in particular 1 or 2 identical or different heteroatoms. Heteroatoms are oxygen, sulfur or nitrogen. Preferred examples are optionally substituted furyl, thiophenyl, pyrazolyl, imidazolyl, 1,2,3- and 1,2,4-triazolyl, oxazolyl, isoxazolyl, thiazolyl, isothiazolyl, 1,2,3-, 1,3,4-, 1,2,4- and 1,2,5-oxadiazolyl, azepinyl, pyrrolyl, isopyrrolyl, pyridyl, piperazinyl, pyridazinyl, pyrimidinyl, pyrazinyl, 1,3,5-, 1,2,4- and 1,2,3-triazinyl, 1,2,4-, 1,2,3-, 1,3,6- and 1,2,6-oxazinyl, oxepinyl, thiepinyl and 1,2,4-diazepinyl.

The optionally substituted radicals of the general formulae may carry one or more, preferably 1 to 3, in particular 1 to 2 identical or different substituents. Preferred examples of substituents are:
alkyl preferably having 1 to 4, in particular 1 or 2 carbon atoms, such as methyl, ethyl, n- and i-propyl and n-, i- and. t-butyl; alkoxy having preferably 1 to 4, in particular 1 or 2 carbon atoms, such as methoxy, ethoxy, n- and i-propyloxy and n-, i- and t-butyloxy; alkylthio having preferably 1 to 4, in particular 1 or 2 carbon atoms, such as methylthio, ethylthio, n- and i-propylthio and n-, i- and t-butylthio; halogenoalkyl having preferably 1 to 4, in particular 1 or 2 carbon atoms and preferably 1 to 5, in particular 1 to 3 halogen atoms, the halogen atoms being identical or different and preferably representing fluorine, chlorine or bromine, in particular fluorine, such as difluoromethyl and trifluoromethyl; hydroxyl; halogen, preferably fluorine, chlorine and bromine, in particular fluorine and chlorine; cyano; nitro; amino; monoalkyl- and dialkylamino having preferably 1 to 4, in particular 1 or 2 carbon atoms per alkyl group, such as methylamino, methylethylamino, n- and i-propylamino and methyl-n-butylamino; acyl radicals such as carboxyl; carboxyl having preferably 2 to 4, in particular 2 or 3 carbon atoms, such as methoxycarbonyl and ethoxycarbonyl; alkylsulfinyl having 1 to 4, in particular 1 to 2 carbon atoms, halogenoalkylsulfinyl having 1 to 4, in particular 1 to 2 carbon atoms and 1 to 5 halogen atoms, such as trifluoromethylsulfinyl; sulfonyl (—$SO_3H$); alkylsulfonyl having preferably 1 to 4, in particular 1 or 2 carbon atoms, such as methylsulfonyl and ethylsulfonyl; halogenoalkylsulfonyl having 1 to 4, in particular 1 to 2 carbon atoms and 1 to 5 halogen atoms, such as trifluoromethylsulfonyl and perfluoro-t,n,s-butylsulfonyl; arylsulfonyl having preferably 6 or 10 aryl carbon atoms, such as phenylsulfonyl; acyl, aryl, aryloxy, hetaryl and hetaryloxy which may themselves carry one of the abovementioned substituents, and the formimino radical

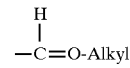

Preferably used are compounds of the formula (I) in which $R^1, R^2, R^{11}$ and $R^{12}$ each represent independently of one another methyl, ethyl, propyl, butyl or phenyl which is optionally substituted by halogen, $C_{1-4}$-alkyl, OH or $C_{1-4}$-alkoxy, and represent benzyl or phenylethyl, each of which is optionally substituted by the radicals given for phenyl;

$R^3$ to $R^{10}$ have the meanings stated above, at least one of these radicals representing benzyl whose phenyl radical is sulfenylated, sulfonylated or phosphorylated.

Especially preferred are compounds of the formula (I) in which $R^1, R^2, R^{11}$ and $R^{12}$ each represent independently of one another methyl, ethyl, propyl, isopropyl or n-, s- or t-butyl, $R^3, R^5, R^7$ and $R^9$ each represent hydrogen, straight-chain $C_{1-5}$-alklyl or branched $C_{4-5}$-alkyl, in particular methyl, ethyl and propyl, which are optionally substituted by $C_{1-4}$-alkoxy, in particular methoxy, ethoxy, imidazolyl, indolyl or $C_{1-4}$-alkylthio, in particular methylthio or ethylthio, and represent isobutyl or s-butyl and further represent phenyl, benzyl, phenylethyl or hetarylmethyl which are optionally substituted by nitro or by a radical —$NR^{13}R^{14}$, $R^{13}$ and $R^{14}$ each representing independently of one another hydrogen or $C_{1-4}$-alkyl, or $R^{13}$ and $R^{14}$ representing together with the N atom attached a 5-, 6- or 7-membered ring which is optionally interrupted by further O, S and N atoms and optionally substituted by $C_{1-4}$-alkyl or by halogen, in particular chlorine.

$R^4, R^6, R^8$ and $R^{10}$ each represent independently of one another hydrogen, methyl, ethyl, n-propyl, n-butyl, vinyl and cyclohexyl which are optionally substituted by methoxy, ethoxy, imidazolyl, indolyl, methylthio or ethylthio and represent isopropyl or s-butyl and further represent optionally halogen-substituted phenyl, benzyl, phenylethyl or hetarylmethyl, at least one of the radicals $R^3$ or $R^{10}$ representing benzyl whose phenyl radical is substituted by one of the abovementioned sulfonyl, sulfenyl or phosphoryl radicals.

The novel aromatic sulfonylated, sulfenylated, thiocyanated or phosphorylated cyclic depsipeptides of the formula (I) and their acid addition salts and metal salt complexes have very good anthelmintic properties and can be employed with preference in the veterinary sector. Surprisingly, they exhibit, in the control of worm diseases, better activity than the prior-art compounds having a similar constitution and used for the same purpose.

The process according to the invention is carried out using halogenosulfonic acids (Hal$SO_3$H), in particular chlorosulfonic acid, and their derivatives, sulfur dihalide, in particular sulfur dichloride and its derivatives, halogenosulfenic acid, in particular chlorosulfenic acid, sulfenyl halides, in particular sulfenyl chlorides, disulfides and sulfuric acid (oleum) as sulfonylating and sulfenylating agents, optionally in a diluent which is inert toward the reagents and optionally in the presence of Lewis acids.

The process according to the invention is carried out using thiocyanate salts, in particular copper(II) thiocyanate and ammonium thiocyanate or thiocyanogen ($(SCN)_2$) as thiocyanating agents, optionally in a diluent which is inert toward the reagents and optionally in the presence of Lewis acids.

The process according to the invention is carried out using phosphorus halides, in particular phosphorus trichloride and phosphorus pentachloride as phosphorylating agents, optionally in a diluent that is inert toward the reagents and optionally in the presence of Lewis acids.

Examples of Lewis acids are: $AlCl_3$, $TiCl_4$, $BF_3$, $OEt_2$, $SbCl_5$, $SnCl_4$, $CuCl_2$, $FeCl_3$, $SnCl_2$, $AgBF_4$, $AgSbF_6$, $AgClO_4$, $LiClO_4$, $Br_2$.

The reaction is carried out at temperatures from 0° to 150° C., preferably at 0° to 80° C., especially preferably at 0° to 60° C.

Suitable diluents are all organic solvents inert toward the reagents. These include in particular aliphatic and aromatic, optionally halogenated hydrocarbons, such as pentane, hexane, heptane, cyclohexane, petroleum ether, benzine, ligroin, benzene, toluene, methylene chloride, ethylene chloride, chloroform, carbon tetrachloride, chlorobenzene and o-dichlorobenzene, ethers, such as diethyl ether and dibutyl ether, glycol dimethyl ether and diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as for example acetonitrile and propionitrile, benzonitrile and glutaronitrile, amides, such as for example dimethylformamide, dimethylacetamide and N-methylpyrrolidone, and also dimethyl sulfoxide, tetramethylene sulfone and hexamethylphosphoric triamide.

The depsipeptides are treated with an excess of reagent (5 to 10 equivalents) and an excess of Lewis acid (15 to 20 equivalents).

After the reaction has ended, the diluent is distilled off and the sulfonylated, sulfenylated, thiocyanated or phosphorylated compounds of the formula (I) are purified in a conventional manner, for example chromatographically.

The active compounds are suitable for controlling pathogenic endoparasites encountered in humans and in animal husbandry and livestock breeding, in productive livestock, breeding stock, zoo animals, laboratory animals, animals used in experiments, and pets, and have low toxicity to warm-blooded animals. They are active against resistant and normally sensitive species and against all or some stages of development. By controlling the pathogenic endoparasites, it is intended to reduce disease, mortality and decreasing performance (for example in the production of meat,. milk, wool, hides, eggs, honey etc.), so that more economical and simpler animal keeping is possible by using the active compounds. The pathogenic endoparasites include Cestodes, Trematodes, Nematodes and Acantocephales in particular:

From the order of the Pseudophyllidea, for example Diphyllobothrium spp., Spirometra spp., Schistocephalus spp., Ligula spp., Bothridium spp., Diplogonoporus Spp., From the order of the Cyclophyllidea, for example Mesocestoides spp., Anoplocephala spp., Paranoplocephala spp., Monieazia spp., Thysanosoma spp., Thysaniezia spp., Avitellina spp., Stilesia spp., Cittotaenia spp., Andyra spp., Bertiella spp., Taenia spp., Echinococcus spp., Hydatigera spp., Davainea spp., Raillietina spp., Hymenolepis spp., Echinolepis spp., Echinocotyle spp., Diorchis spp., Dipylidium spp., Joyeuxiella spp., Diplopylidium spp..

From the subclass of the Monogenea, for example Gyrodactylus spp., Dactylogyrus spp., Polystoma spp..

From the subclass of the Digenea, for example Diplostomum spp., Posthodiplostomum spp., Schistosoma spp., Trichobilharzia spp., Ornithobilharzia spp., Austrobilharzia spp., Gigantobilharzia spp., Leucochloridium spp., Brachylaima spp., Echinostoma spp., Echinoparyphium spp., Echinochasmus spp., Hypoderaeum spp., Fasciola spp., Fasciolides spp., Fasciolopsis spp., Cyclocoelum spp., Typhlocoelum spp., Paramphistomum spp., Calicophoron spp., Cotylophoron spp., Gigantocotyle spp., Fischoederius spp., Gastrothylacus spp., Notocotylus spp., Catatropis spp., Plagiorchis spp., Prosthogonimus spp., Dicrocoelium spp., Eurytrema spp., Troglotrema spp., Paragonimus spp., Collyriclum spp., Nanophyetus spp., Opisthorchis spp., Clonorchis spp., Metorchis spp., Heterophyes spp., Metagonimus spp..

From the order of the Enoplida, for example Trichuris spp., Capillaria spp., Trichomosoides spp., Trichinella spp.

From the order of the Rhabditida, for example Micronema spp., Strongyloides spp..

From the order of the Strongylida, for example Strongylus spp., Triodontophorus spp., Oesophagodontus spp., Trichonema spp., Gyalocephalus spp., Cylindropharynx spp., Poteriostomum spp., Cyclococercus spp., Cylicostephanus spp., Oesophagostomum spp., Chabertia spp., Stephanurus spp., Ancylostoma spp., Uncinaria spp., Bunostomum spp., Globocephalus spp., Syngamus spp., Cyathostoma spp., Metastrongylus spp., Dictyocaulus spp., Muellerius spp., Protostrongylus spp., Neostrongylus spp., Cystocaulus spp., Pneumostrongylus spp., Spicocaulus spp., Elaphostrongylus spp., Parelaphostrongylus spp., Crenosoma spp., Paracrenosoma spp., Angiostrongylus spp., Aelurostrongylus spp., Filaroides spp., Parafilaroides spp., Trichostrongylus spp., Haemonchus spp., Ostertagia spp., Marshallagia spp., Cooperia spp., Nematodirus spp., Hyostrongylus spp., Obeliscoides spp., Amidostomum spp., Ollulanus spp..

From the order of the Oxyurida, for example Oxyuris spp., Enterobius spp., Passalurus spp., Syphacia spp., Aspiculuris spp., Heterakis spp..

From the order of the Ascaridia, for example Ascaris spp., Toxascaris spp., Toxocara spp., Parascaris spp., Anisakis spp., Ascaridia spp..

From the order of the Spirurida, for example Gnathostoma spp., Physaloptera spp., Thelazia spp., Gongylonema spp., Habronema spp., Parabronema spp., Draschia spp., Dracunculus spp..

From the order of the Filariida, for example Stephanofilaria spp., Parafilaria spp., Setaria spp., Loa spp., Dirofilaria spp., Litomosoides spp., Brugia spp., Wuchereria spp., Onchocerca spp..

From the order of the Gigantorhynchida, for example Filicollis spp., Moniliformis spp., Macracanthorhynchus spp., Prosthenorchis spp..

The livestock and breeding stock include mammals, such as, for example, cattle,. horses, sheep, pigs, goats, camels, water buffalo, donkeys, rabbits, fallow deer, reindeer, fur-bearing animals, such as, for example, minks, chinchilla or racoon, birds, such as, for example chickens, geese, turkeys or ducks, freshwater fish and sea fish, such as, for example, trout, carp and eels, reptiles and insects, such as, for example, honey bee and silkworm.

The laboratory and test animals include mice, rats, guinea pigs, golden hamsters, dogs and cats.

The pets include dogs and cats.

Administration can be effected prophylactically as well as therapeutically.

The active substances are administered, either directly or in the form of suitable preparations, enterally, parenterally, dermally, nasally, by treating the habitat or with the aid of shaped articles containing the active compound, such as, for example, strips, plates, tapes, collars, ear tags, limb bands or marking devices.

Enteral administration of the active compounds is effected for example orally in the form of powders, tablets, capsules, pastes, drinks, granules, solutions, suspensions and emulsions which can be applied orally, boluses, medicated feed or drinking water.

Dermal application is effected, for example, in the form of dipping, spraying, or pouring-on and spotting-on. Parenteral administration is effected, for example, in the form of injection (intramuscular, subcutaneous, intravenous or intraperitoneal) or by implants.

Suitable preparations include:

Solutions, such as solutions for injection, oral solutions, concentrates for oral administration after dilution, solutions for use on the skin or in body cavities, pour-on formulations, gels;

Emulsions and suspension for oral or dermal administration and for injection; semi-solid preparations;

Formulations in which the active compound is incorporated in a cream base or in an oil-in-water or water-in-oil emulsion base;

Solid preparations, such as powders, premixes or concentrates, granules, pellets, tablets, boluses, capsules; aerosols and inhalants, shaped articles containing the active compound.

Solutions for injection are administered intravenously, intramuscularly and subcutaneously.

Solutions for injection are prepared by dissolving the active compound in a suitable solvent and, if desired, adding additives, such as solubilizers, acids, bases, buffer salts, antioxidants, or preservatives. The solutions are sterile-filtered and decanted into containers.

Suitable solvents include: physiologically acceptable solvents, such as water, alcohols, such as ethanol, butanol, benzyl alcohol, glycerol, propylene glycol, polyethylene glycols and N-methyl-pyrrolidone, and their mixtures.

If appropriate, the active compounds can also be dissolved in physiologically acceptable vegetable or synthetic oils which are suitable for injection.

Suitable solubilizers include: solvents which facilitate the dissolution of the active compound in the main solvent or which prevent precipitation of the active compound. Examples of solubilizers are polyvinylpyrrolidone, polyethoxylated castor oil and polyethoxylated sorbitan esters.

The following are preservatives: benzyl alcohol, trichlorobutanol, p-hydroxybenzoic esters or n-butanol.

Oral solutions are administered directly. Concentrates are first diluted to the administration concentration and then administered orally. Oral solutions and concentrates are prepared as described above in the case of the solutions for injection, sterile procedures not being necessary.

Solutions for use on the skin are applied drop by drop, smoothed on, rubbed in, splashed on or sprayed on. These solutions are prepared as described above in the case of the solutions for injection.

It may be advantageous to add thickeners in the preparation process. The following are thickeners: inorganic thickeners, such as bentonites, colloidal silica, aluminum monostearate, or organic thickeners, such as cellulose derivatives, polyvinyl alcohols and their copolymers, acrylates and methacrylates.

Gels are applied to the skin or smoothed on or introduced into body cavities. Gels are prepared by adding such an amount of thickener to solutions which have been prepared as described in the solutions for injection that a clear composition is formed which has an ointment-like consistency. The thickeners used are the thickeners indicated further above.

Pour-on and spot-on formulations are poured or splashed onto limited areas of the skin, the active compound penetrating the skin and acting systemically.

Pour-on and spot-on formulations are prepared by dissolving, suspending or emulsifying the active compound in suitable solvents or solvent mixtures which are tolerated by the skin. If appropriate, other auxiliaries, such as colorants, absorption promoters, antioxidants, photostabilizers or tackifiers.

Suitable solvents include: water, alkanols, glycols, polyethylene glycols, polypropylene glycols, glycerol, aromatic alcohols, such as benzyl alcohol, phenylethanol or phenoxyethanol, esters, such as ethyl acetate, butyl acetate or benzyl benzoate, ethers, such as alkylene glycol alkyl ethers, such as dipropylene glycol monomethyl ether or diethylene glycol mono-butyl ether, ketones, such as acetone or methyl ethyl ketone, aromatic and/or aliphatic hydrocarbons, vegetable or synthetic oils, DMF, dimethylacetamide, N-methylpyrrolidone, or 2,2-dimethyl-4-oxy-methylene-1,3-dioxolane.

Colorants are all colorants which can be dissolved or suspended and which are approved for use in animals.

Examples of absorption promoters are DMSO, spreading oils, such as isopropyl myristate, dipropylene glycol pelargonate, silicone oils, fatty acid esters, triglycerides or fatty alcohols.

The following are antioxidants: sulfites or metabisulfites, such as potassium metabisulfite, ascorbic acid, butylhydroxytoluene, butylhydroxyanisole or tocopherol.

Example of photostabilizers are novantisolic acid.

Tackifiers are, for example, cellulose derivatives, starch derivatives, polyacrylates or natural polymers such as alginates or gelatin.

Emulsions can be administered orally, dermally or as injections.

Emulsions are either the water-in-oil type or the oil-in-water type.

They are prepared by dissolving the active compound either in the hydrophobic or in the hydrophilic phase and by homogenizing this phase with the solvent of the other phase, with the aid of suitable emulsifiers and, if appropriate, other auxiliaries, such as colorants, absorption promoters, preservatives, antioxidants, photostabilizers, and viscosity-increasing substances.

Suitable hydrophobic phases (oils) include: paraffin oils, silicone oils, natural vegetable oils such as sesame seed oil, almond oil or castor oil, synthetic triglycerides, such as caprylic/capric acid biglyceride, a triglyceride mixture with vegetable fatty acids of chain length $C_{8-12}$ or other specifically selected natural fatty acids, mixtures of partial glycerides of saturated or unsaturated fatty acids which may also contain hydroxyl groups, and mono- and diglycerides of the $C_8/C_{10}$-fatty acids.

Fatty acid esters, such as ethyl stearate, di-n-butyladipate, hexyl laurate, dipropylene glycol pelargonate, esters of a branched fatty acid having a medium chain length with saturated fatty alcohols of chain length $C_{16}$-$C_{18}$, isopropyl myristate, isopropyl palmitate, caprylic/capric esters of saturated fatty alcohols of chain length $C_{12}$-$C_{18}$, isopropyl stearate, oleyl oleate, decyl oleate, ethyl oleate, ethyl lactate, waxy fatty acid esters such as artificial duck uropygial fat, dibutyl phthalate, diisopropyl adipate, ester mixtures related to the latter, etc.

Fatty alcohols, such as isotridecyl alcohol, 2-octyldodecanol, cetylstearyl alcohol or oleyl alcohol.

Fatty acids, such as, for example, oleic acid and its mixtures.

Suitable hydrophilic phases include: water, alcohols, such as, for example, propylene glycol, glycerol, sorbitol and their mixtures.

Suitable emulsifiers include: non-ionic surfactants, for example polyethoxylated castor oil, polyethoxylated sorbitan monooleate, sorbitan monostearate, glycerol monostearate, polyoxyethyl stearate or alkylphenol polyglycol ethers;

Ampholytic surfactants, such as disodium N-lauryl-β-iminodipropionate or lecithin;

Anionic surfactants, such as Na lauryl sulfate, fatty alcohol ether sulfates, and the monoethanolamine salt of mono/dialkylpolyglycol ether orthophosphoric ester;

Cationic surfactants, such as cetyltrimethylammonium chloride.

Suitable other auxiliaries include: substances which increase the viscosity and stabilize the emulsion, such as carboxymethylcellulose, methylcellulose and other cellulose and starch derivatives, polyacrylates, alginates, gelatin, gum arabic, polyvinylpyrrolidone, polyvinylalcohol, methylvinyl ether/maleic anhydride copolymers, polyethylene glycols, waxes, colloidal silica, or mixtures of the listed substances.

Suspensions can be administered orally, dermally or as an injection. They are prepared by suspending the active compound in a liquid excipient, if appropriate with the addition of other auxiliaries, such as wetting agents, colorants, absorption promoters, preservatives, antioxidants and photostabilizers.

Suitable liquid excipients include all homogeneous solvents and solvent mixtures.

Suitable wetting agents (dispersants) include the surfactants indicated further above.

Suitable other auxiliaries include those indicated further above.

Semi-solid preparations can be administered orally or dermally. They are only distinguished from the above-described suspensions and emulsions by their higher viscosity.

To prepare solid preparations, the active compound is mixed with suitable excipients, if appropriate with the addition of auxiliaries, and the mixture is formulated as desired.

Suitable excipients include all physiologically acceptable solid inert substances. Suitable for this purpose are inorganic and organic substances. Inorganic substances are, for example, common salt, carbonates, such as calcium carbonate, hydrogencarbonates, aluminum oxides, silicas, clays, precipitated or colloidal silica, and phosphates.

Organic substances are, for example, sugars, cellulose, foodstuffs and animal feeds, such as powdered milk, animal meals, cereal meals, coarse cereal meals and starches.

Auxiliaries are preservatives, antioxidants and colorants which have already been mentioned further above.

Other suitable auxiliaries are lubricants and gliding agents, such as, for example, magnesium stearate, stearic acid, talc, bentonites, disintegrants, such as starch or crosslinked polyvinylpyrrolidone, binders, such as, for example, starch, gelatin or linear polyvinylpyrrolidone, and dry binders, such as microcrystalline cellulose.

In the preparations, the active compounds can also be present in mixtures with synergists or other active compounds which are active against pathogenic endoparasites. Examples of such active compounds are L-2,3,5,6-tetrahydro-6-phenylimidazothiazole, benzimidazole carbamates, praziquantel, pyrantel or febantel.

Ready-to-use preparations contain the active compound in concentrations of 10 ppm to 20 percent by weight, preferably from 0.1 to 10 percent by weight.

Preparations which are diluted before use contain the active compound in concentrations of 0.5 to 90 per cent by weight, preferably from 5 to 50 percent by weight.

In general, it has proved advantageous to administer amounts of about 1 to about 100 mg of active compound per kg of body weight per day, to achieve effective results.

EXAMPLE A

Nematodes in vivo test

Haemonchus contortus/sheep

Sheep experimentally infected with Haemonchus contortus were treated after the end of the pre-patency period of the parasites. The active compounds were administered orally as pure active compound in gelatin capsules (p.o.) or injected intravenously as a solution (i.v.).

The degree of effectiveness is determined by quantitatively counting the worm eggs excreted with the feces, before and after treatment.

Complete cessation of the excretion of eggs after a treatment means that the worms have been expelled or are so severely damaged that they can no longer produce any eggs (effective dose).

Active compounds examined and effective doses are shown in the table below.

| | Effective dose in mg/kg | |
|---|---|---|
| Example No. | p.o | i.v. |
| 1 | 0.5 | 0.5 |

The preparation of the active compounds according to the invention is shown in the examples below.

PREPARATION EXAMPLES

1. General Chlorosulfonylation Procedure

A solution of a depsipeptide (0.523 mmol) in dichloromethane is treated with chlorosulfonic acid (37.3 mmol) at 0° C., stirred for 2 hours at 0° C. and for 2 hours at room temperature. At 0° C., the reaction mixture is added dropwise to acetone (50 ml). At 0° C., the mixture is then treated with morpholine (79.4 mmol) and stirring is continued at 60° C. for 12 hours. After this time, the solution is concentrated, taken up in water and extracted with dichloromethane (3 x). The combined organic extracts are dried over $Na_2SO_4$ and concentrated. The residue is purified by column chromatography using tert-butyl methyl ether/cyclohexane/methanol (10:1:0.4) as eluent. This yields depsipeptides of the formula (I) in which the substituents have the meanings given below.

2. General Sulfonylation Procedure

The respective depsipeptide (1.05 mmol) is added to cold oleum at a temperature of 0° C. (20%, 25 ml) and stirred at this temperature for 1 to 2 hours. The mixture is then poured onto 250 ml of ice and neutralized with $Ba(OH)_2$. The residue is filtered off and washed three times with water. The filtrate is concentrated to a volume of 5 to 10 ml and chromatographed using a strongly acidic ion exchanger (50 g) and water. Concentration of the solvent yields the depsipeptides of the formula (I).

3. General Phosphorylation Procedure

Sulfonyl chloride (3 equivalents) is added dropwise to a suspension of $PCl_3$ (3 equivalents), $AlCl_3$ (3 equivalents) and the depsipeptide in carbon tetrachloride which had been cooled to −10° C. Stirring is continued at 70° C. for 1 minute, and excess $SO_2Cl_2$ is distilled off under reduced pressure. The residue is taken up in carbon tetrachloride and, with cooling, slowly treated with an excess of an alcohol or an amine. The reaction mixture is washed several times with a little water, dried over $Na_2SO_4$ and concentrated. Silica gel column chromatography of the residue affords the depsipeptides of the formula (I).

4. General Sulfenylation Procedure

At room temperature, $SbCl_5$, (0.15 mmol) and $AgSbF_6$ (0.15 mmol) are initially charged in 2 ml of 1,2-dichloroethane. A solution of dimethyl disulfide (0.5 mmol) in dichloromethane (2 ml) is then added dropwise and, finally, a solution of the depsipeptide (1.0 mmol) in 1,2-dichloroethane is added dropwise. The reaction mixture is heated at reflux temperature for 3 to 6 hours and, after cooling, the reaction is quenched with sat. aqueous $NaHCO_3$ solution. The mixture is washed three times with water, dried over $Na_2SO_4$ and concentrated. Silica gel column chromatography of the residue affords the depsipeptides of the formula (I).

5. General Thiocyanation Procedure

A solution of the depsipeptide (1.0 mmol) in glacial acetic acid (5 ml) is treated with $Ca(SCN)_2$ (2 to 5 mmol) and stirred at 60° C. After cooling and filtration, the solution is diluted with water, neutralized with $NaHCO_3$ solution and extracted with ethyl acetate. Silica gel column chromatography of the residue affords the depsipeptides of the formula (I).

| No. | $R^1$ | $R^2$ | $R^3$ | $R^4$ | $R^5$ | $R^6$ | $R^7$ | $R^8$ | $R^9$ | $R^{10}$ | $R^{11}$ | $R^{12}$ | FAB-MS |
|---|---|---|---|---|---|---|---|---|---|---|---|---|---|
| 1 | Me | Me | $SO_2$—N(morpholino) | $^i$Bu | Me | $^i$Bu | $SO_2$—N(morpholino) | $^i$Bu | Me | $^i$Bu | Me | Me | 1247 (100, M$^+$ + H) |
| 2 | " | " | $SO_2$—N(piperidine-3,5-diol) | " | " | " | $SO_2$—N(piperidine-3,5-diol) | " | " | " | " | " | |
| 3 | " | " | $SO_2$—N(piperidine-3,5-diOMe) | " | " | " | $SO_2$—N(piperidine-3,5-diOMe) | " | " | " | " | " | |
| 4 | " | " | $SO_2$—N(Me)(Me) | " | " | " | $SO_2$—N(Me)(Me) | " | " | " | " | " | |
| 5 | " | " | $SO_2$—N(piperazine) | " | " | " | $SO_2$—N(piperazine) | " | " | " | " | " | |
| 6 | " | " | $SO_2$—N(N-Me-piperazine) | " | " | " | $SO_2$—N(N-Me-piperazine) | " | " | " | " | " | |
| 7 | " | " | $SO_2$—NH—$CH_2$-(tetrahydrofuran-2-yl) | " | " | " | $SO_2$—NH—$CH_2$-(tetrahydrofuran-2-yl) | " | " | " | " | " | |
| 8 | " | " | $SO_2$—N(Me)—$CH_2$-(tetrahydrofuran-2-yl) | " | " | " | $SO_2$—N(Me)—$CH_2$-(tetrahydrofuran-2-yl) | " | " | " | " | " | |
| 9 | " | " | $SO_2$—OMe | " | " | " | $SO_2$—OMe | " | " | " | " | " | |
| 10 | " | " | $SO_2$—OPh | " | " | " | $SO_2$—OPh | " | " | " | " | " | |
| 11 | " | " | $SO_2$—OBu | " | " | " | $SO_2$—OBu | " | " | " | " | " | |

-continued

| No. | R¹ | R² | R³ | R⁴ | R⁵ | R⁶ | R⁷ | R⁸ | R⁹ | R¹⁰ | R¹¹ | R¹² | FAB-MS |
|---|---|---|---|---|---|---|---|---|---|---|---|---|---|
| 12 | " | " | SO₂—OCH₂—(tetrahydrofuran-2-yl) | " | " | " | SO₂—OCH₂—(tetrahydrofuran-2-yl) | " | " | " | " | " | |
| 13 | " | " | SO₂—O—(CH₂)₂—OMe | " | " | " | SO₂—O—(CH₂)₂—OMe | " | " | " | " | " | |
| 14 | " | " | SO₂—O—(CH₂)₂—N(morpholino) | " | " | " | SO₂—O—(CH₂)₂—N(morpholino) | " | " | " | " | " | |
| 15 | " | " | SO₂—OH | " | " | " | SO₂—OH | " | " | " | " | " | |
| 16 | " | " | S-CN | " | " | " | S-CN | " | " | " | " | " | |
| 17 | " | " | S-Me | " | " | " | S-Me | " | " | " | " | " | |
| 18 | " | " | S-Ph | " | " | " | S-Ph | " | " | " | " | " | |
| 19 | " | " | S-pyridyl | " | " | " | S-pyridyl | " | " | " | " | " | |
| 20 | " | " | S-CH₂—CH₂—OMe | " | " | " | S-CH₂—CH₂—OMe | " | " | " | " | " | |
| 21 | " | " | S-CH₂—CH₂—NMe₂ | " | " | " | S-CH₂—CH₂—NMe₂ | " | " | " | " | " | |
| 22 | " | " | P(=O)(OEt)—OEt | " | " | " | P(=O)(OEt)—OEt | " | " | " | " | " | |
| 23 | " | " | P(=O)(OPh)—OPh | " | " | " | P(=O)(OPh)—OPh | " | " | " | " | " | |
| 24 | " | " | P(=O)(O—CH₂—CH₂—OMe)—O—CH₂—CH₂—OMe | " | " | " | P(=O)(O—CH₂—CH₂—OMe)—O—CH₂—CH₂—OMe | " | " | " | " | " | |
| 25 | " | " | P(=O)(O—CH₂—CH₂—N(morpholino))—O—CH₂—CH₂—N(morpholino) | " | " | " | P(=O)(O—CH₂—CH₂—N(morpholino))—O—CH₂—CH₂—N(morpholino) | " | " | " | " | " | |
| 26 | " | " | P(=O)(NEt₂)—NEt₂ | " | " | " | P(=O)(NEt₂)—NEt₂ | " | " | " | " | " | |
| 27 | " | " | P(=O)(NPh₂)—NPh₂ | " | " | " | P(=O)(NPh₂)—NPh₂ | " | " | " | " | " | |
| 28 | " | " | P(=O)(N(CH₂—CH₂—OMe)₂)—N(CH₂—CH₂—OMe)₂ | " | " | " | P(=O)(N(CH₂—CH₂—OMe)₂)—N(CH₂—CH₂—OMe)₂ | " | " | " | " | " | |
| 29 | " | " | P(=O)(N(CH₂—CH₂—NMe₂)₂)—N(CH₂—CH₂—NMe₂)₂ | " | " | " | P(=O)(N(CH₂—CH₂—NMe₂)₂)—N(CH₂—CH₂—NMe₂)₂ | " | " | " | " | " | |

| No. | R¹ | R² | R³ | R⁴ | R⁵ | R⁶ | R⁷ | | R⁸ | R⁹ | R¹⁰ | R¹¹ | R¹² | FAB-MS |
|---|---|---|---|---|---|---|---|---|---|---|---|---|---|---|
| 30 | " | " | 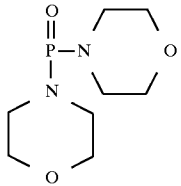 | " | " | " | 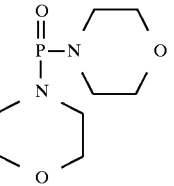 | | " | " | " | " | " | " |

We claim:

1. A cyclic depsipeptide compound having 6 to 24 ring atoms, and comprising at least one phenyl or benzyl radical which is sulfonylated, sulfenylated, thiocyanated or phosphorylated, said cyclic depsipeptide compound being synthesized from α-hydroxycarboxylic acids and α-amino acids.

2. A compound of the formula (I):

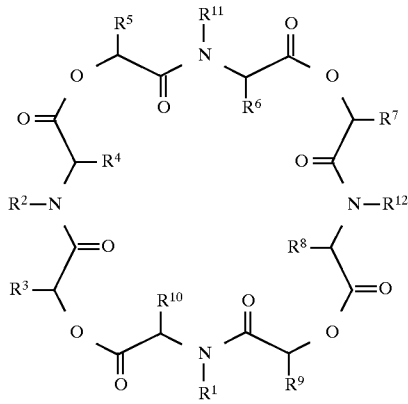

and in which $R^1, R^2, R^{11}$ and $R^{12}$ independently represent hydrogen or optionally substituted $C_{1-8}$-alkyl, $C_{3-6}$-cycloalkyl, aralkyl or aryl;

at least one of $R^3, R^4, R^5, R^6, R^7, R^8, R^9$ or $R^{10}$ represents phenyl or benzyl, both of which are substituted by a sulfonyl, sulfenyl, thiocyanato or phosphoryl group; and the remainder of $R^3, R^4, R^5, R^6, R^7, R^8, R^9$, or $R^{10}$ are defined as follows:

$R^3, R^5, R^7$ and $R^9$ independently represent hydrogen, straight-chain or branched $C_{1-8}$-alkyl, which is optionally substituted by a substituent selected from the group consisting of hydroxyl, $C_{1-4}$alkoxy, aryloxyl, hetaryloxyl, carboxyl, carboxamido, —OCONH$_2$, imidazolyl, indolyl, guanidino, —SH, and $C_{1-4}$-alkylthio, or $R^3, R^5, R^7$ and $R^9$ additionally independently represent optionally substituted aryl or aralkyl; and $R^4, R^6, R^8$ and $R^{10}$ independently represent hydrogen, or straight-chain or branched $C_{1-8}$-alkyl, $C_{2-6}$-alkenyl or $C_{3-7}$-cycloalkyl, each of which is optionally substituted by a substituent selected from the group consisting of hydroxyl, $C_{1-4}$alkoxy, carboxyl, carboxamido, imidazolyl, indolyl, guanidino, —SH and $C_{1-4}$alkylthio, or $R_4, R_6, R_8$ and $R_{10}$ additionally independently represent optionally substituted aryl or aralkyl.

3. The compound according to claim 2, wherein at least one of $R^3$, $R^4, R^5, R^6, R^7, R^8, R^9$ or $R^{10}$ represents benzyl, which is are substituted by a sulfonyl, sulfenyl, thiocyanato or phosphoryl group.

4. The compound according to claim 2, wherein at least one of $R^3$ or $R^7$ represents benzyl, which is substituted by a sulfonyl, sulfenyl, thiocyanato or phosphoryl radical selected from the group consisting of those of the formulae:

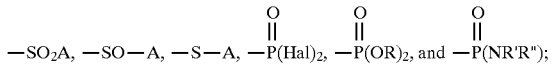

in which

Hal represents halogen;

A represents halogen, hydroxyl, —OR,—NH$_2$,—NHR' or —NR'R";

R represents optionally substituted alkyl, alkenyl, alkinyl, aryl or aralkyl;

R' represents optionally substituted alkyl, aryl or aralkyl; and

R" represents optionally substituted alkyl, aryl or aralkyl; or

R' and R" together with the nitrogen atom to which they are bonded together form an optionally substituted heterocyclic radical, which may contain further ring heteroatoms selected from the group consisting of N, O and S.

5. The compound according to claim 2, of the formula (I):

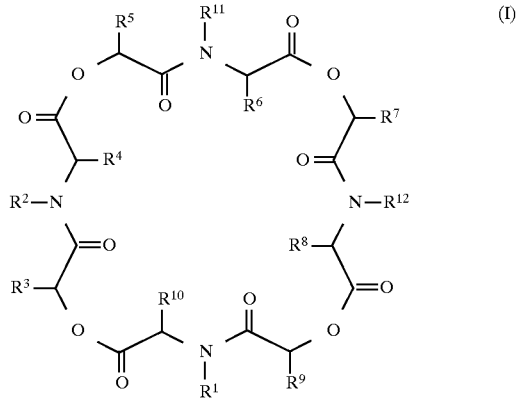

and in which $R^1, R^2, R^{11}$ and $R^{12}$ independently represent hydrogen, or $C_{1-8}$-alkyl, $C_{3-6}$-cycloalkyl, aralkyl or aryl, each of which is optionally substituted by one or more substituents independently selected from the group consisting of: $C_{1-4}$-alkyl, $C_{1-4}$-alkyl, $C_{1-4}$-alkylamino, di-$C_{1-4}$alkylamino, carboxyl, $C_{2-4}$-alkoxycarbonyl, $C_{1-4}$alkylsulfinyl, halogeno-$C_{1-4}$-alkysulfinyl, sulfonyl, $C_{1-4}$-alkylsulfonyl, or halogeno-$C_{1-4}$-alkysulfonyl, or aryl, aryloxy, hetaryl or hetaryloxy, each of which is optionally substituted by $C_{1-4}$-alkoxy, $C_{1-4}$alkylthio, halogeno-$C_{1-4}$-alkyl, hydroxyl, halogen, cyano, nitro, amino, $C_{1-4}$-alkylamino, di-$C_{1-4}$-alkylamino, carboxyl, $C_{2-4}$-alkoxycarbonyl, $C_{1-4}$-alkysulfinyl, halogeno-$C_{1-4}$-alkysulfinyl, sulfonyl, $C_{1-4}$-alkysulfonyl, or halogeno-$C_{1-4}$-alkysulfonyl, and —CH=N—O—Alkyl;

at least one of $R^3, R^4, R^5, R^6, R^7, R^8, R^9$ or $R^{10}$ represents phenyl or benzyl, both of which are substituted by a sulfonyl, sulfenyl, thiocyanato or phosphoryl group;

and the remainder of $R^3, R^4, R^5, R^6, R^7, R^8, R^9$ or $R^{10}$ are defined as follows:

$R^3, R^5, R^7$ and $R^9$ independently represent hydrogen, straight-chain or branched $C_{1-8}$alkyl, which is optionally substituted by a substituent selected from the group consisting of hydroxyl, $C_{1-4}$-alkoxy, aryloxy, hetaryloxy, carboxyl, carboxamido, —OCONH$_2$, imidazolyl, indolyl, guanidino, —SH, and $C_{1-4}$-alkylthio, or $R^3$, $R^5$, $R^7$ and $R^9$ additionally independently represent aryl or aralkyl, both of which are optionally substituted by one or more substituents independently selected from the group consisting of: $C_{1-4}$-alkyl, $C_{1-4}$-alkoxy, $C_{1-4}$-alkylthio halogeno-$C_{1-4}$-alkyl, hydroxyl, halogen, cyano, nitro, amino, $C_{1-4}$-alkylamino, di-$C_{1-4}$-alkylamino, carboxyl, $C_{2-4}$-alkoxycarbonyl, $C_{1-4}$-alkylsulfinyl, halogeno-$C_{1-4}$-alkysulfinyl, sulfonyl, $C_{1-4}$-alkylsulfonyl, or halogeno-$C_{1-4}$-alkylsulfonyl, or aryl, aryloxy, hetaryl or hetaryloxy, each of which is optionally substituted by $C_{1-4}$alkyl, $C_{1-4}$-alkoxy, $C_{1-4}$-alkylthio, halogeno-$C_{1-4}$alkyl, hydroxyl, halogen, cyano, nitro, amino, $C_{1-4}$alkylamino, di-$C_{1-4}$alkylamino, carboxyl, $C_{2-4}$alkoxycarbonyl, $C_{1-4}$-alkylsulfinyl, halogeno-$C_{1-4}$-alkysulfinyl, sulfonyl, $C_{1-4}$-alkylsulfonyl, or halogeno-$C_{1-4}$-alkylsulfonyl, and —CH=N—O—Alkyl; and $R^4, R^6, R^8$ and $R^{10}$ independently represent hydrogen, or straight-chain or branched $C_{1-8}$-alkyl, $C_{2-6}$-alkenyl or $C_{3-7}$-cycloalkyl, each of which is optionally substituted by a substituent selected from the group consisting of hydroxyl, $C_{1-4}$-alkoxy, carboxyl, carboxamido, imidazolyl, indolyl, guanidino, —SH and $C_{1-4}$-alkylthio, or $R^4$, $R^6$, $R^8$ and $R^{10}$ additionally independently represent aryl or aralkyl, both of which are optionally substituted by ne or more substituents independently selected from the group consisting of: $C_{1-4}$-alkyl, $C_{1-4}$-alkoxy, $C_{1-4}$-alkylthio, halogeno-$C_{1-4}$-alkyl., hydroxyl, halogen, cyano, nitro, amino, $C_{1-4}$-alkylamino, di-$C_{1-4}$-alkylamino, carboxyl, $C_{2-4}$alkoxycarbonyl, $C_{1-4}$-alkylsulfinyl, halogeno-$C_{1-4}$-alkylsulfinyl, sulfonyl, $C_{-1-4}$-alkylsulfonyl, or halogeno-$C_{1-4}$-alkysulfonyl, or aryl, aryloxy, hetaryl or hetaryloxy, each of which is optionally substituted by $C_{1-4}$-alkyl, $C_{1-4}$alkoxy, $C_{1-4}$-alkylthio, halogeno-$C_{1-4}$alkyl, hydroxyl, halogen, cyano, nitro, amino, $C_{1-4}$alkylamino, di-$C_{1-4}$-alkylamino, carboxyl, $C_{2-4}$-alkoxycarbonyl,$C_{1-4}$-alkylsulfinyl, halogeno-$C_{1-4}$alkylsulfinyl, sulfonyl, $C_{-1-4}$-alkylsulfonyl, or halogeno-$C_{1-4}$-alkylsulfonyl, and —CH=N—O—Alkyl.

6. An encoparasiticidal composition comprising an endoparasiticidally effective amount of the compound according to claim 1 and a pharmaceutically acceptable carrier.

7. An endoparasiticidal composition comprising an endoparasiticidally effective amount of the compound according to claim 2 and a pharmaceutically acceptable carrier.

8. An endoparasiticidal composition comprising an endoparasiticidally effective amount of the compound according to claim 3 and a pharmaceutically acceptable carrier.

9. An endoparasiticidal composition comprising an endoparasiticidally effective amount of the compound according to claim 4 and a pharmaceutically acceptable carrier.

10. An endoparasiticidal composition comprising an endoparasiticidally effective amount of the compound according to claim 5 and a pharmaceutically acceptable carrier.

11. A method of combating endoparasites comprising administering to a human or an animal an endoparasiticidally effective amount of the compound according to claim 1.

12. A method of combating endoparasites comprising administering human or an animal an endoparasiticidally effective amount of the compound according to claim 2.

13. A method of combating endoparasites comprising administering human or an animal an endoparasiticidally effective amount of the compound according to claim 3.

14. A method of combating endoparasites comprising administering to a human or an animal an endoparasiticidally effective amount of the compound according to claim 4.

15. A method of combating endoparasites comprising administering human or an animal an endoparasiticidally effective amount of the compound according to claim 5.

16. A process for preparing a compound according to claim 11, said process comprising reacting a cyclic depsipeptide with a sulfonylating, sulfenylating, thiocyanating or phosphorylating agent optionally in the presence of a catalyst, auxiliary and/or diluent, wherein said cyclic depsipeptide has 6 to 24 ring atoms, and comprises at least one phenyl or benzyl radical that is not sulfonylated, sulfenylated, thiocyanated or phosphorylated, and said cyclic depsipeptide is synthesized from α-hydroxycarboxylic acids and α-amino acids.

17. The process according to claim 16, which is for the preparation of a compound of the formula (I):

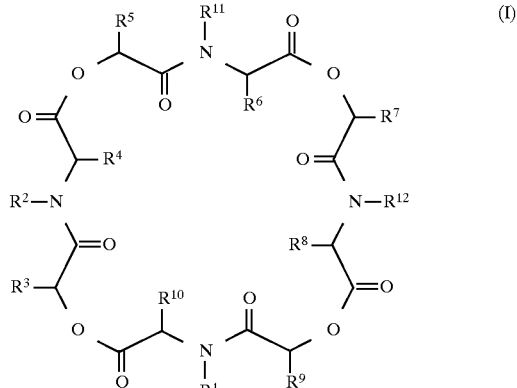

in which
$R^1, R^2, R^{11}$ and $R^{12}$ independently represents hydrogen or optionally substituted $C_{1-8}$alkyl, $C_{3-6}$-cycloalkyl, aralkyl or aryl;
at least one of $R^3, R^4, R^5, R^6, R^7, R^8, R^9$ or $R^{10}$ represents phenyl or benzyl both of which are substituted by a sulfonyl, sulfenyl, thiocyanato or phosphoryl group;
and the remainder of $R^3, R^4, R^5, R^6, R^7, R^8, R^9$ are defined as follows:
$R^3, R^5, R^7$ and $R^9$ independently represent hydrogen, straight-chain or branched $C_{1-8}$-alkyl, which is optionally substituted by a substituent selected from the group consisting of hydroxyl, $C_{1-4}$alkoxy, aryloxy, hetaryloxy, carboxyl, carboxamido, —OCONH$_2$, imidazolyl, indolyl, guanidino, —SH, and $C_{1-4}$-alkylthio, or $R^3,R^5,R^7$ and $R^9$ additionally independently represent optionally substituted aryl or aralkyl; and $R^4,R^6,R^8, R^{10}$ independently represent hydrogen, or straight-chain or branched $C_{1-8}$alkyl, $C_{2-6}$-alkenyl or $C_{3-7}$-cycloalkyl, each of which is optionally substituted by a substituent selected from the group consisting of hydroxyl, $C_{1-4}$-alkoxy, carboxyl, carboxamido, imidazolyl, indolyl, guanidino, —SH and $C_{1-4}$-alkylthio, or $R^4,R^6,R^8$ and $R^{10}$ additionally independently represent optionally substituted aryl or aralkyl.

18. The process according to claim 17, which is for the preparation of a compound of the formula (I), wherein at least one of $R^3,R^4,R^5,R^6,R^7,R^8,R^9$ or $R^{10}$ represents benzyl, which is are substituted by a sulfonyl, sulfenyl, thiocyanato or phosphoryl group.

19. The process according to claim 17, which is for the preparation of a compound of the formula (I), wherein at least one of $R^3$ or $R^7$ represents benzyl, which is substituted by a sulfonyl, sulfenyl, thiocyanato or phosphoryl radical selected from the group consisting of those of the formulae:

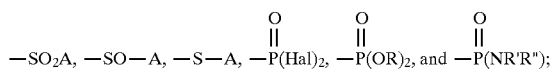

$-SO_2A, -SO-A, -S-A, -P(Hal)_2, -P(OR)_2,$ and $-P(NR'R'')$;

in which

Hal represents halogen;

A represents halogen, hydroxyl, —OR, —NH$_2$, —NHR' or —NR'R'';

R represents optionally substituted alkyl, alkenyl, alkinyl, aryl or aralkyl;

R' represents optionally substituted alkyl, aryl or aralkyl; and

R'' represents optionally substituted alkyl, aryl or aralkyl; or

R' and R'' together with the nitrogen atom to which they are bonded together form an optionally substituted heterocyclic radical, which may contain further ring heteroatoms selected from the group consisting of N, O and S.

20. The process according to claim 17, which is for the preparation of a compound of the formula (I):

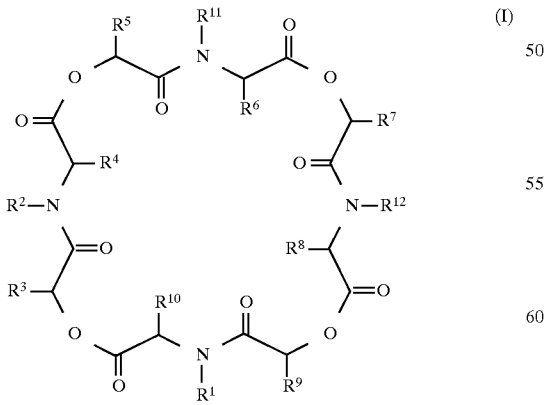

in which $R^1,R^2,R^{11}$ and $R^{12}$ independently represent hydrogen, or $C_{1-8}$-alkyl, $C_{3-6}$-cycloalkyl, aralkyl or aryl, each of which is optionally substituted by one or more substituents independently selected form the group consisting of: $C_{1-4}$-alkyl, $C_{1-4}$ alkylthio, halogeno-$C_{1-4}$-alkyl, hydroxyl, halogen, cyano, nitro, amino, $C_{1-4}$alkylamino, di-$C_{1-4}$alkylamino, carboxyl, $C_{2-4}$alkoxycarbonyl, $C_{1-4}$alkysulfinyl, halogeno-$C_{1-4}$-alkylsulfinyl, sulfonyl, $C_{1-4}$-alkylsulfonyl, or halogeno-$C_{1-4}$-alkylsulfonyl, or aryl, aryloxy, hetaryl or hetaryloxy, each of which is optionally substituted by $C_{1-4}$-alkyl, $C_{1-4}$-alkoxy, $C_{1-4}$-alkylthio, halogeno-$C_{1-4}$-alkyl, hydroxyl, halogen, cyano, nitro, amino, $C_{1-4}$-alkylamino, di-$C_{1-4}$-alkylamino, carboxyl, $C_{2-4}$-alkoxycarbonyl, $C_{1-4}$-alkylsulfinyl, halogeno-$C_{1-4}$-alkylsulfinyl, sulfonyl, $C_{1-4}$-alkylsulfonyl, or halogeno-$C_{1-4}$-alkylsulfonyl, and —CH=N—O—Alkyl;

at least one of $R^3,R^4,R^5,R^6,R^7,R^8,R^9$ or $R^{10}$ represents phenyl or benzyl, both of which are substituted by a sulfonyl, sulfenyl, thiocyanato or phosphoryl group;

and the remainder of $R^3,R^4,R^5,R^6,R^7,R^8,R^9$ or $R^{10}$ are defined as follows:

$R^3,R^5,R^7$ and $R^9$ independently represent hydrogen, straight-chain or branched $C_{1-8}$-alkyl, which is optionally substituted by a substituent selected from the group consisting of hydroxyl, $C_{1-4}$-alkoxy, aryloxy, hetaryloxy, carboxyl, carboxamido, —OCONH$_2$, imidazolyl, indolyl, guanidino, —SH, and $C_{1-4}$-alkylthio, or $R^3,R^5,R^7$ and $R^9$ additionally independently represent aryl or aralkyl, both of which are optionally substituted by one or more substituents independently selected from the group consisting of: $C_{1-4}$-alkyl, $C_{1-4}$-alkoxy, $C_{1-4}$-alkylthio, halogeno-$C_{1-4}$-alkyl, hydroxyl, halogen, cyano, nitro, amino, $C_{1-4}$-alkylamino, di-$C_{1-4}$-alkylamino, carboxyl, $C_{2-4}$-alkoxycarbonyl, $C_{1-4}$-alkylsulfinyl, halogeno-$C_{1-4}$-alkylsulfinyl, sulfonyl, $C_{1-4}$-alkylsulfonyl, or halogeno-$C_{1-4}$-alkylsulfonyl, or aryl, aryloxy, hetaryl or hetaryloxy, each of which is optionally substituted by $C_{1-4}$-alkyl, $C_{1-4}$-alkoxy, $C_{1-4}$-alkylthio, halogeno-$C_{1-4}$-alkyl, hydroxyl, halogen, cyano, nitro, amino, $C_{1-4}$-alkylamino, di-$C_{1-4}$-alkylamino, carboxyl, $C_{2-4}$-alkoxycarbonyl, $C_{1-4}$-alkylsulfinyl, halogeno-$C_{1-4}$-alkylsulfinyl, sulfonyl, $C_{1-4}$-alkylsulfonyl, or halogeno-$C_{1-4}$-alkylsulfonyl, and —CH=N—O—Alkyl; and $R^4,R^6,R^8$ and $R^{10}$ independently represent hydrogen, or straight-chain or branched $C_{1-8}$-alkyl, $C_{2-6}$-alkenyl or $C_{3-7}$-cycloalkyl, each of which is optionally substituted by a substituent by a substituent selected from the group consisting of hydroxyl, $C_{1-4}$-alkoxy, carboxyl, carboxamido, imidazolyl, indolyl, guanidino, —SH and $C_{1-4}$-alkylthio, or $R^4,R^6,R^8$ and $R^{10}$ additionally independently represent aryl or aralkyl, both of which are optionally substituted by one or more substituents independently selected from the group consisting of: $C_{1-4}$-alkyl, $C_{1-4}$-alkoxy, $C_{1-4}$- alkylthio, halogeno-$C_{1-4}$-alkyl, hydroxyl, halogen, cyano, nitro, amino, $C_{1-4}$-alkylamino, di-$C_{1-4}$-alkylamino, carboxyl, $C_{2-4}$-alkoxycarbonyl, $C_{1-4}$-alkylsulfinyl, halogeno-$C_{1-4}$-alkylsulfinyl, sulfonyl, $C_{1-4}$-alkylsulfonyl, or halogeno-$C_{1-4}$-alkylsulfonyl, or aryl, aryloxy, hetaryl or hetaryloxy, each of which is optionally substituted by $C_{1-4}$-alkyl, $C_{1-4}$-alkoxy, $C_{1-4}$-alkylthio, halogeno-$C_{1-4}$alkyl, hydroxyl, halogen, cyano, nitro, amino, $C_{1-4}$-alkylamino, di-$C_{1-4}$alkylamino, carboxyl, $C_{2-4}$-alkoxycarbonyl, $C_{1-4}$-alkylsulfinyl, halogeno-$C_{1-4}$-alkylsulfinyl, sulfonyl, $C_{1-4}$alkylsulfonyl, or halogeno-$C_{1-4}$alkylsulfonyl, and —CH=N—O—Alkyl.

* * * * *